US008755490B2

(12) United States Patent
Takamura

(10) Patent No.: US 8,755,490 B2
(45) Date of Patent: Jun. 17, 2014

(54) X-RAY IMAGING DEVICE

(75) Inventor: Shoji Takamura, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 372 days.

(21) Appl. No.: 13/262,136

(22) PCT Filed: Apr. 7, 2009

(86) PCT No.: PCT/JP2009/057142
§ 371 (c)(1),
(2), (4) Date: Sep. 29, 2011

(87) PCT Pub. No.: WO2010/116494
PCT Pub. Date: Oct. 14, 2010

(65) Prior Publication Data
US 2012/0027174 A1   Feb. 2, 2012

(51) Int. Cl.
*H05G 1/38* (2006.01)
(52) U.S. Cl.
USPC ............... 378/96; 378/62; 378/97; 378/98.7; 378/108
(58) Field of Classification Search
USPC ............ 378/62, 96, 97, 98.7, 98.8, 108–112, 378/165
See application file for complete search history.

(56) References Cited

U.S. PATENT DOCUMENTS

| 4,896,343 | A  | * | 1/1990 | Saunders ........................ 378/95 |
|-----------|----|---|--------|------------------------------------------|
| 5,949,811 | A  | * | 9/1999 | Baba et al. .................... 378/108 |
| 5,949,848 | A  | * | 9/1999 | Gilblom ....................... 378/98.8 |
| 6,208,710 | B1 | * | 3/2001 | Nagai .......................... 378/108 |
| 6,259,767 | B1 | * | 7/2001 | Neumann et al. ............. 378/151 |
| 6,292,537 | B1 | * | 9/2001 | Zimmermann ............... 378/108 |
| 6,502,984 | B2 | * | 1/2003 | Ogura et al. .................. 378/206 |
| 6,516,098 | B2 | * | 2/2003 | Nonaka ......................... 382/274 |
| 6,920,201 | B2 | * | 7/2005 | Maack et al. ................. 378/116 |
| 6,934,362 | B2 | * | 8/2005 | Scheuering ................... 378/108 |
| 6,942,385 | B2 | * | 9/2005 | Fadler et al. .................. 378/205 |
| 7,054,412 | B2 | * | 5/2006 | Scheuering ................... 378/108 |
| 7,209,543 | B2 | * | 4/2007 | Strommer ...................... 378/97 |

(Continued)

FOREIGN PATENT DOCUMENTS

| JP | 59-044798 | 3/1984 |
| JP | S59-044798 | 3/1984 |
| JP | 06-277204 | 10/1994 |
| JP | 2778079 | 7/1998 |

OTHER PUBLICATIONS

"Office Action of Japan Counterpart Application", issued on Nov. 6, 2012, with English translation thereof, p. 1-p. 5, in which the listed references were cited.

*Primary Examiner* — Allen C. Ho
(74) *Attorney, Agent, or Firm* — J.C. Patents

(57) ABSTRACT

Disclosed is an X-ray imaging device with which X-ray exposure will not be stopped due to the backup time, causing underexposure, in phototimer imaging, because the body of the subject is thick. A database unit (18) stores a database showing the relationships among a variety of subject (M) body thicknesses (t), X-ray parameters, and imaging times. A search processor (16) searches the aforementioned database for data matching X-ray parameters stored in a parameter storage unit (15) and body thicknesses (t) calculated by a body thickness measurement unit (17), and requests the corresponding imaging time. If the imaging time is longer than the backup time set by an X-ray controller (12), the search processor (16) instructs the X-ray controller (12) to extend the backup time to the imaging time.

2 Claims, 2 Drawing Sheets

(56) References Cited

U.S. PATENT DOCUMENTS

| | | | |
|---|---|---|---|
| 7,298,823 B2 * | 11/2007 | Bernhardt et al. | 378/97 |
| 7,372,943 B2 * | 5/2008 | Bernhardt | 378/98.12 |
| 7,519,155 B2 * | 4/2009 | Mollus et al. | 378/108 |
| 7,528,376 B2 * | 5/2009 | Shoji | 250/370.09 |
| 7,545,915 B2 * | 6/2009 | Hess et al. | 378/108 |
| 7,660,390 B2 * | 2/2010 | Bernhardt et al. | 378/98.8 |
| 7,792,243 B2 * | 9/2010 | Strommer | 378/37 |

* cited by examiner

X-RAY IMAGING DEVICE

CROSS-REFERENCE TO RELATED APPLICATION

This application is a 371 national phase application of international application of PCT application serial no. PCT/JP2009/057142, filed on Apr. 7, 2009. The entirety of the above-mentioned patent application is hereby incorporated by reference and made a part of this specification.

BACKGROUND OF THE INVENTION

1. Field of the Invention

The invention relates to an X-ray imaging device and particularly relates to the backup time of an X-ray imaging device having an automatic exposure control (phototimer) function.

2. Description of Related Art

An X-ray imaging device, for example, is formed by an X-ray tube that irradiates a subject by X ray; an X-ray detector including a flat panel detector (FPD) for imaging the X ray that passes through the subject; a phototimer that automatically controls exposure time of the X ray; a measurement unit for measuring the body thickness of the subject; and a control console having an operating panel for operating the foregoing components.

The X ray that penetrates the subject is converted into an electrical signal by a phototimer detector. The phototimer includes an integrator for integrating the electrical signal; and a comparator for comparing an output signal of the integrator that is in proportion to concentration with a concentration reference signal. In phototimer imaging, an X-ray shutoff signal is outputted from the comparator to stop X-ray exposure when the output signal of the integrator is greater than the concentration reference signal, so as to complete the X-ray imaging with proper exposure. Even though the imaging time can be automatically determined to achieve proper exposure, if the set backup time is shorter than the imaging time, the X-ray exposure is stopped due to the backup time.

During phototimer imaging, for instance, the phototimer detector may detect X ray that mainly passes through the bones of the subject. As a consequence, the electrical signals inputted into the integrator become fewer, and the time for the output signal of the integrator to exceed the concentration reference signal becomes longer than the backup time. In that case, the X-ray exposure is stopped due to the backup time to prevent overexposure.

Furthermore, an X-ray imaging device has been provided (see Reference 1, for example), which automatically sets the tube voltage, the tube current, and the imaging time based on the measured body thickness of the subject and does not require the operator to input imaging parameters according to different subjects. With the help of the X-ray imaging device, inexperienced users can also operate the device to obtain acceptable imaging results. In addition, mistakes in inputting imaging parameters and unnecessary X-ray exposure can be prevented, and an image that correctly matches the imaging parameters can be obtained.

Reference 1: Japanese Patent Application Laid-open No. H06-277204

SUMMARY OF THE INVENTION

Problem to be Solved by the Invention

When using the conventional X-ray imaging device to perform phototimer imaging, the X ray passing through the subject may be reduced if the subject has a thicker body, and the output signal of the phototimer detector is decreased accordingly. As a result, the imaging time (i.e. the time for the output signal of the integrator to exceed the concentration reference signal and for the comparator to output the X-ray shutoff signal) becomes longer. If the set backup time is a fixed value and the subject has a thicker body, the backup time may be shorter than the imaging time. When the X-ray exposure is stopped due to the backup time, underexposure occurs.

Technical Solution

To solve the aforementioned problems, the invention provides an X-ray imaging device that includes an X-ray tube for irradiating a subject with an X ray; an X-ray detector for imaging the X ray that penetrates the subject; a phototimer for controlling the X-ray exposure time; an X-ray controller for controlling X-ray exposure; a measurement unit for measuring the body thickness of the subject; a control console for controlling the aforementioned elements, a storage unit and an alarm unit. The storage unit is for storing a database showing a relationship between a body thickness of the subject, an X-ray parameter, and an imaging time and/or the relationship between the body thickness of the subject, the X-ray parameter, and the imaging time in each imaged part of the subject. The alarm unit for setting off an alarm when the backup time, which is set by the X-ray controller as a time limit of the X-ray exposure, is shorter than the imaging time shown in the database in a case when the body thickness measured from the subject's body approaches the body thickness in the data base and an X-ray parameter set by the control console approaches the X-ray parameter in the datatbase.

To solve the aforementioned problems, the X-ray imaging device comprises an extension unit for extending the backup time when the backup time is shorter than the imaging time shown in the database in the case when the body thickness measured from the subject's body approaches the body thickness in the database and the X-ray parameter set by the control console approaches the X-ray parameter in the database. Accordingly, if the subject has a thicker body, the X-ray exposure will not be stopped due to the backup time.

Effects of the Invention

According to the invention, an X-ray exposure does not be stopped due to the backup time. When the subject has a thicker body, the problem of underexposure does not occur. Therefore, improper X-ray imaging can be avoided, and the burden on the operator and the subject can be reduced.

DESCRIPTION OF EMBODIMENTS

The body thickness t of the subject is calculated by a body thickness measurement unit based on an equation, $t=(L-A-B)$. L represents a distance from a focal point of an X-ray tube to a contact surface between a bucky unit and the subject. The distance L is controlled by a control unit that drives a tube bulb holding device, and a value of the distance L is transmitted from the control unit to the body thickness measurement unit. A represents a distance between the focal point and a datum plane of a distance sensor, which is a known and fixed value and is stored by the body thickness measurement unit. B represents a distance from the datum plane of the distance sensor to a body surface of the subject, and the distance B is measured by the distance sensor by ultrasonics and transmitted to the body thickness measurement unit.

Embodiment

Figure 1:
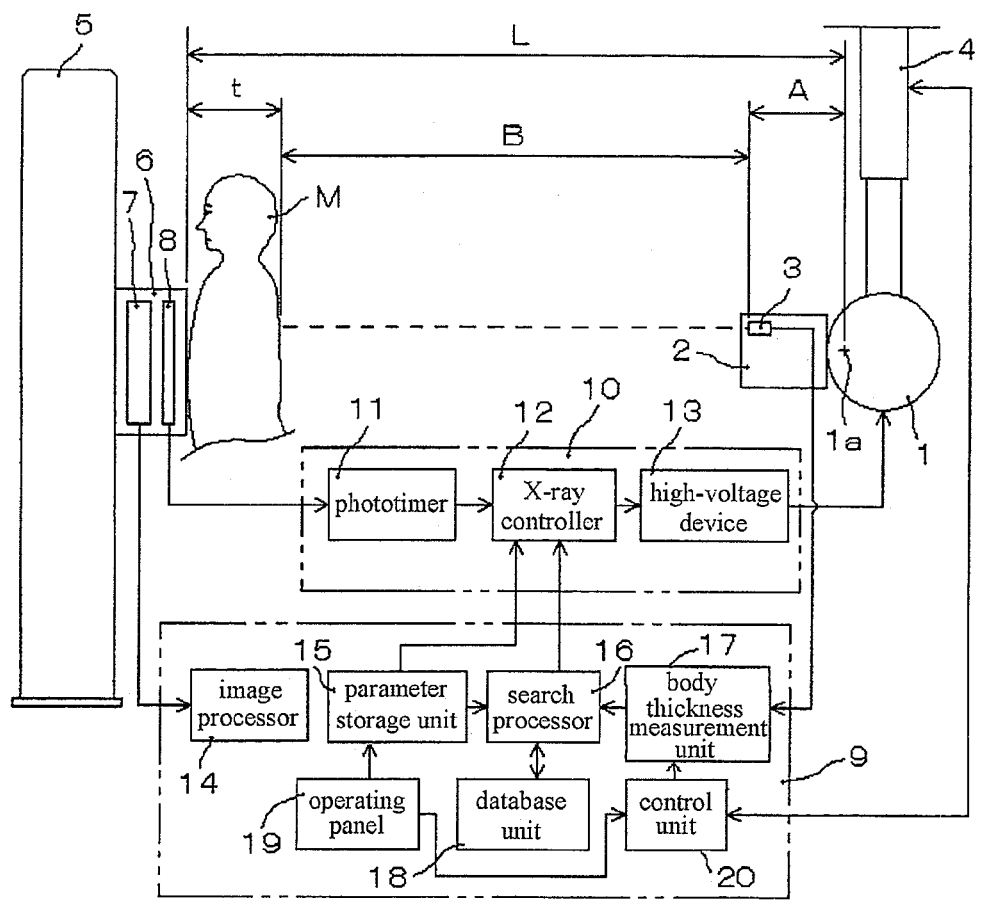
FIG. 1 is a structural view illustrating an X-ray imaging device according to an embodiment of the invention.
Figure 2:
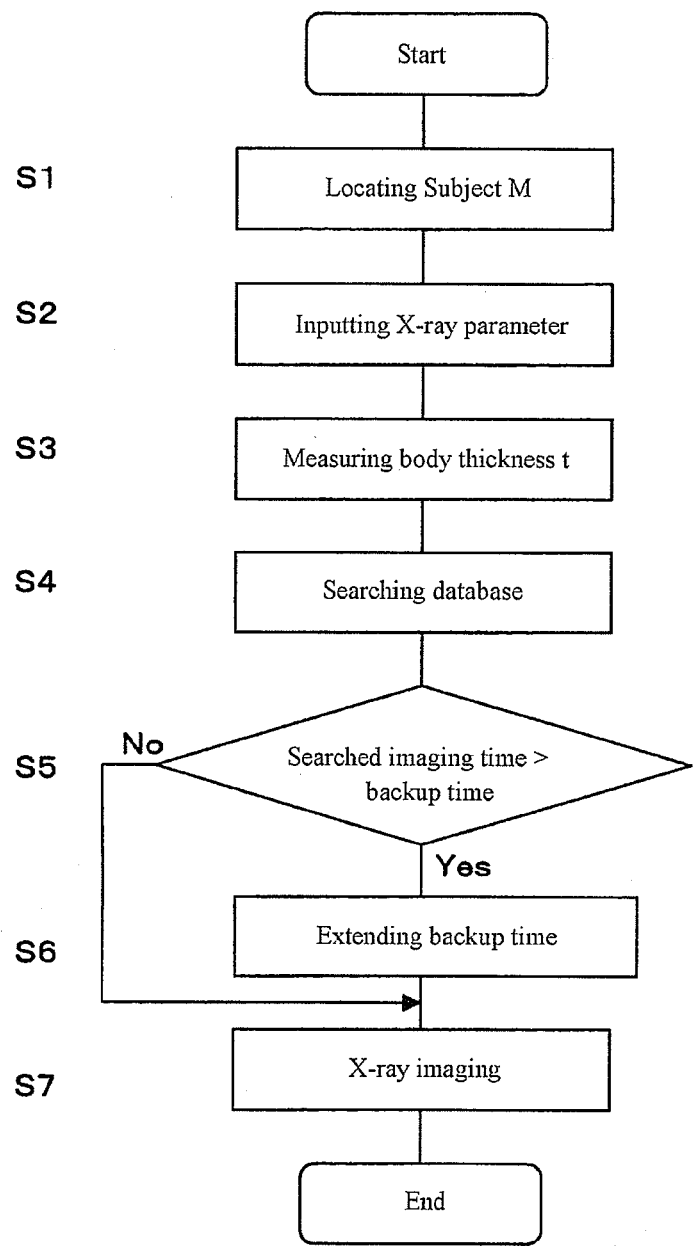
FIG. 2 is a flowchart showing the operations of an X-ray imaging device according to an embodiment of the invention.

The embodiments of the invention are described below with reference to FIG. 1 and FIG. 2. Specifically, FIG. 1 is a structural view illustrating an X-ray imaging device in one embodiment of the invention. FIG. 2 is a flowchart of the operations of an X-ray imaging device in an embodiment of the invention.

As shown in FIG. 1, the X-ray imaging device includes an X-ray tube 1, a collimator 2, an ultrasonic distance sensor 3, a tube bulb holding device 4, an upright stand 5, an X-ray generator 10, and a control console 9. The X-ray tube 1 has a focal point 1a and irradiates a subject M by X ray. The collimator 2 is supported by the X-ray tube 1 for determining an irradiation field of the X ray. The ultrasonic distance sensor 3 is disposed on an inner side of the collimator 2 for measuring the distance B to the body surface of the subject M. The tube bulb holding device 4 holds the X-ray tube 1 and allows the X-ray tube 1 to move in a horizontal direction or a vertical direction. In addition, a bucky unit 6, which includes a phototimer detector 8 and a X-ray detector 7, is disposed on the upright stand 5 and is movable in the vertical direction. The X-ray generator 10 is used to control X-ray exposure. And, the control console 9 is used to control the aforementioned units, measure body thickness, process image, and extend a backup time when required.

The X-ray generator 10 comprises a phototimer 11, an X-ray controller 12, and a high-voltage device 13. The functions of the foregoing units are described below.

The phototimer detector 8 converts the X ray that passes through the subject M into an electrical signal and transmits the electrical signal to the phototimer 11. The phototimer 11 includes an integrator and a comparator, wherein the integrator integrates the electrical signal, and the comparator compares an output signal of the integrator, which is proportional to concentration, with a concentration reference signal. During a phototimer imaging, the comparator outputs an X-ray shutoff signal when the output signal of the integrator becomes greater than the concentration reference signal. When receiving the X-ray shutoff signal, the X-ray controller 12 instructs the high-voltage device 13 to stop the X ray, so as to complete the X-ray imaging with proper exposure. Even though the imaging time can be automatically determined to achieve proper exposure, if the backup time set by the X-ray controller 12 is shorter than the imaging time, the X-ray exposure is stopped due to the backup time. In a case when the imaging time is longer than the set backup time due to the subject M has a thicker body, the invention extends the backup time to prevent underexposure.

The control console 9 comprises an image processor 14, a parameter storage unit 15, a search processor 16, a body thickness measurement unit 17, a database unit 18, an operating panel 19, and a control unit 20. The functions of the foregoing units are described respectively below.

The X ray that passes through the subject M also penetrates the phototimer detector 8 and is incident to the X-ray detector 7, which is formed by an FPD, for example. The X ray is converted into an electrical signal and inputted in the image processor 14 to be imaged and displayed on a display (not shown).

The body thickness measurement unit 17 calculates the body thickness t of the subject M based on the equation, $t=(L-A-B)$. L represents a distance from the focal point 1a of the X-ray tube 1 to a contact surface between the bucky unit 6 and the subject M. The distance L is controlled by the control unit 20 that drives the tube bulb holding device 4, and the distance L is sent to the body thickness measurement unit 17 from the control unit 20. A represents a distance between the focal point 1a and a datum plane of the distance sensor 3. The distance A is a known and fixed value and is stored by the body thickness measurement unit 17. B represents a distance from the datum plane of the distance sensor 3 to the body surface of the subject M. The distance B is measured by the distance sensor 3 and transmitted to the body thickness measurement unit 17.

The database unit 18 stores a database that shows the relationships among a variety of the body thicknesses t of the subject M, X-ray parameters, and imaging times, wherein the X-ray parameters consist of tube voltages and tube currents. The search processor 16 searches the database for data, which corresponds to the X-ray parameters inputted into the parameter storage unit 15 through the operating panel 19 and the body thickness t measured by the body thickness measurement unit 17, and obtains the corresponding imaging time. If the imaging time is longer than the backup time set by the X-ray controller 12, the search processor 16 instructs the X-ray controller 12 to extend the backup time to the imaging time.

With reference to FIG. 2, the following describes the operations/steps for carrying out the phototimer imaging of the X-ray imaging device in the embodiment of the invention. In Step (represented by "S" in the following) 1, an operator puts the subject M in a way that the chest of the subject M is in contact with the bucky unit 6. In S2, the operator inputs the X-ray parameters, e.g. tube currents and tube voltages, through the operating panel 19, and the X-ray parameters are stored in the parameter storage unit 15. In S3, the ultrasonic distance sensor 3 measures the distance B and transmits the distance B to the body thickness measurement unit 17. The body thickness measurement unit 17 calculates the body thickness t and transmits the body thickness t to the search processor 16, wherein the body thickness t is calculated by substituting the distance A, the distance L transmitted from the control unit 20, and the distance B into the equation: $t=(L-A-B)$.

In S4, the search processor 16 searches the database in the database unit 18 for data that corresponds to the X-ray parameters stored in the parameter storage unit 15 and the transmitted body thickness t, and acquires the corresponding imaging time. In S5, the search processor 16 compares the obtained imaging time with the backup time stored in the X-ray controller 12. If the backup time is shorter than the imaging time, S6 is performed. If the backup time is longer than the imaging time, S7 is performed. In S6, the search processor 16 instructs the X-ray controller 12 to extend the backup time of the current X-ray imaging to the imaging time obtained by search, and the X-ray controller 12 extends the backup time of the current X-ray imaging accordingly. In S7, the X-ray controller 12 performs X-ray exposure by the high-voltage device 13 based on the X-ray parameters stored in the parameter storage unit 15 and stops the X-ray exposure to end the imaging when receiving an X-ray shutoff signal from the phototimer 11.

Therefore, in the invention, if the body of the subject M is thicker, the X-ray exposure is not stopped due to the backup time, and the problem of underexposure does not occur. Since improper X-ray imaging is prevented, the burden on the operator and the subject M can be reduced.

It should be noted that the standing-type imaging device shown in the figures is merely an example of the invention. The invention is also applicable to a horizontal imaging device, wherein the subject M is put on a horizontally slidable bed and the X ray is irradiated from the top to perform the imaging. Herein, the body thickness t of the subject M is calculated by substituting a distance between the focal point 1a and the bed for the distance L, substituting a distance between the focal point 1a and the datum plane of the ultrasonic distance sensor 3 for the distance A, and substituting a distance between the datum plane and the body surface of the subject M for the distance B.

Moreover, the figures illustrate phototimer imaging that can automatically control exposure. However, instead of using phototimer imaging, in other embodiments of the invention, X-ray imaging can also be carried out by the imaging time that is acquired by searching a database based on the X-ray parameters inputted by the operator and the measured body thickness t. Therefore, an image of correct exposure can be obtained regardless of the body thickness t. Therefore, the invention includes various embodiments and should not be construed as limited to the disclosure of the affixed figures.

INDUSTRIAL APPLICABILITY

This invention relates to an X-ray imaging device. In particular, this invention is applicable to the backup time of an X-ray imaging device with phototimer function.

The scope of the invention is defined by the attached claims not by the above detailed descriptions.

What is claimed is:

1. An X-ray imaging device, comprising:
an X-ray tube irradiating a subject by X ray;
an X-ray detector imaging the X ray that passes through the subject;
a phototimer receiving an electrical signal from a phototimer detector and controlling an X-ray exposure time;
an X-ray controller controlling an X-ray exposure;
a measurement unit measuring a body thickness of the subject;
a control console controlling the X-ray tube, the X-ray detector, the phototimer, the X-ray controller and the measurement unit; and
a storage unit storing a database showing a plurality of relationships between a body thickness of the subject, an X-ray parameter, and an imaging time and/or a plurality of relationships between the body thickness of the subject, an X-ray parameter, and an imaging time in each imaged part,
wherein the control console comprises a search processor, comparing a backup time and the imagining time and regulating the backup time according to a comparison result of comparing the backup time and the imagining time, the backup time is set by the X-ray controller as a time limit of the X-ray exposure, the imaging time is shown in the database in a case when the body thickness measured from a body of the subject approaches the body thickness in the database and an X-ray parameter set by the control console approaches the X-ray parameter in the database.

2. The X-ray imaging device as claimed in claim 1, wherein the search processor extends the backup time when the backup time is shorter than the imaging time.

* * * * *